(12) United States Patent
Habib et al.

(10) Patent No.: US 6,628,990 B1
(45) Date of Patent: Sep. 30, 2003

(54) APPLICATOR FOR MICROWAVE RADIATION TREATMENT

(75) Inventors: Nagy Adly Habib, London (GB); Alan John Sangster, Scotland (GB)

(73) Assignee: Imperial College Innovations, Ltd., London (GB)

( * ) Notice: Subject to any disclaimer, the term of this patent is extended or adjusted under 35 U.S.C. 154(b) by 0 days.

(21) Appl. No.: 09/762,285

(22) PCT Filed: Aug. 4, 1999

(86) PCT No.: PCT/BG99/02559
§ 371 (c)(1),
(2), (4) Date: Apr. 6, 2001

(87) PCT Pub. No.: WO00/07666
PCT Pub. Date: Feb. 17, 2000

(30) Foreign Application Priority Data

Aug. 5, 1998 (GB) .............................................. 9817078

(51) Int. Cl.⁷ .................................................. A61F 2/00
(52) U.S. Cl. ......................................... 607/101; 607/99
(58) Field of Search ............................. 607/101, 99, 49

(56) References Cited

U.S. PATENT DOCUMENTS

| | | | |
|---|---|---|---|
| 4,974,587 A | | 12/1990 | Turner et al. ................ 128/399 |
| 5,370,675 A | * | 12/1994 | Edwards et al. ............ 607/101 |
| 5,472,441 A | * | 12/1995 | Edwards et al. .............. 606/41 |
| 5,500,012 A | * | 3/1996 | Brucker et al. ............. 607/122 |
| 5,629,678 A | | 5/1997 | Gargano et al. ............ 340/573 |
| 5,704,352 A | | 1/1998 | Tremblay et al. ........... 128/630 |
| 5,833,603 A | | 11/1998 | Kovacs et al. .............. 128/630 |
| 5,963,132 A | | 10/1999 | Yoakum ................... 340/572.1 |
| 6,015,386 A | | 1/2000 | Kensey et al. .............. 600/486 |
| 6,053,873 A | | 4/2000 | Govari et al. ............... 600/505 |

* cited by examiner

Primary Examiner—Roy D. Gibson
Assistant Examiner—Aaron Roane
(74) Attorney, Agent, or Firm—Oppenheimer Wolff & Donnelly LLP

(57) ABSTRACT

A device for generating locallised heating in a selected body tissue is disclosed. The device comprises an applicator including a source of microwave radiation and an array of retractable needles arranged so as to extend from one face of the applicator and, in operation, to confine the irradiated microwave energy field emanating from the applicator. The use of this device in surgical procedures is described.

5 Claims, 2 Drawing Sheets

APPLICATOR FOR MICROWAVE RADIATION TREATMENT

This invention relates to a device for use in the surgical treatment of human or non-human animals. In particular, it is concerned with a device for use in controlling excessive bleeding from severed tissue during surgical procedures, especially on the patient's liver.

It is well known that raising the temperature of body tissue tends to reduce blood flow within the tissue. If the temperature is raised by 20–30° C. above normal, blood flow within the tissue is greatly diminished.

In surgical procedure performed on deep-seated body tissues and organs, e.g. the liver, blood loss from severed tissue can be a serious problem. There is an obvious need for a device which can assist in limiting such blood loss and, as indicated above, this can be achieved by means of the application of heat. Widespread heating can be achieved relatively easily, but this is not desirable. Very localised heating is required in order to minimise damage to surrounding tissues. In liver surgery, local heating of the liver is ideally required in a tissue volume approximately 5 cm long by 2 cm wide by 4 cm deep; this volume is centred on the planned point of incision. Furthermore, it is important for the local elevation of temperature to be achieved quickly just prior to commencing the surgical procedure.

U.S. Pat. No. 4,974,587 discloses a device for heating biological tissues, comprising a microwave generator and an array of electro-magnetic EM energy applicators being microwave antennae or LCF capacitance type electrodes attached to an envelope filled with a high dielectric fluid. The electrodes are inserted into tubes on the surface of the envelope. This insertion process may be controlled by a positioning unit.

EP 0 073 709 discloses a device for generating localised heating in body tissues, the source of microwave being in the form of a cylindrical waveguide.

The present invention aims to provide a device for providing localised heating of a selected region of body tissue prior to surgical incision of that tissue.

According to one aspect of the present invention, there is provided a device for generating localised heating in a selected body tissue, wherein the said device comprises an applicator including a source of microwave radiation, characterised in that:

(A) the source of microwave radiation is in the form of a waveguide;

(B) the applicator includes an array of retractable needles arranged so as to extend from one face of the applicator;

(C) the waveguide and the array of needles, when extended, define a volume whose dimensions correspond to those of the tissue volume which is to be heated; and (D) in operation, the array of needles serves to confine the irradiated microwave energy field emanating from the applicator.

The invention also provides the use of the device as defined above for restricting the loss of blood during a surgical procedure on the human or animal body.

According to another aspect of the present invention, there is provided, in the surgical treatment of the human or animal body, a method of controlling excessive bleeding, the method comprising inserting an array of needles into the tissue or organ being treated; and applying microwave energy to the region undergoing treatment for a time sufficient to raise the temperature of said tissue or organ by 20–30 degrees C.

Conveniently, the source of microwave radiation is in the form of a rectangular waveguide whose dimensions correspond to those of the tissue volume which is to be heated. The waveguide is preferably generally rectangular in form, the array of retractable needles being positioned around the periphery of the waveguide.

The device may include a needle advance mechanism including a collar to which the needles are secured; movement of said collar may be actuated by a solenoid mechanism.

In operation of the device, the needles will be advanced from the body of the applicator into the tissue which is to be heated so that the needles function as a extension of the waveguide; in this way, the applicator will direct the required microwave energy into the appropriate tissue volume prior to surgery. When the heating process is completed, the needles are retracted back into the body of the applicator.

Generally, the needles will be disposed mutually parallel, they can conveniently be formed of steel.

Theoretical calculations show that, in order to raise the temperature of body tissues by 30° C., an applicator operating with 100% efficiency would need to deliver about 10 watts of microwave power, assuming that the volume to be heated is 40 cm. For a typical biological tissue such as muscle, this temperature rise would be achieved in approximately 10 minutes. If the source is increased in energy to 500 watt, and if the applicator is assumed to be about 80% efficient, the time taken to achieve this required temperature increase is approximately 15 seconds.

For a better understanding of the invention, and to show how the same may be carried into effect, reference will now be made, by way of example, to the accompanying drawings, in which.

Figure 1:
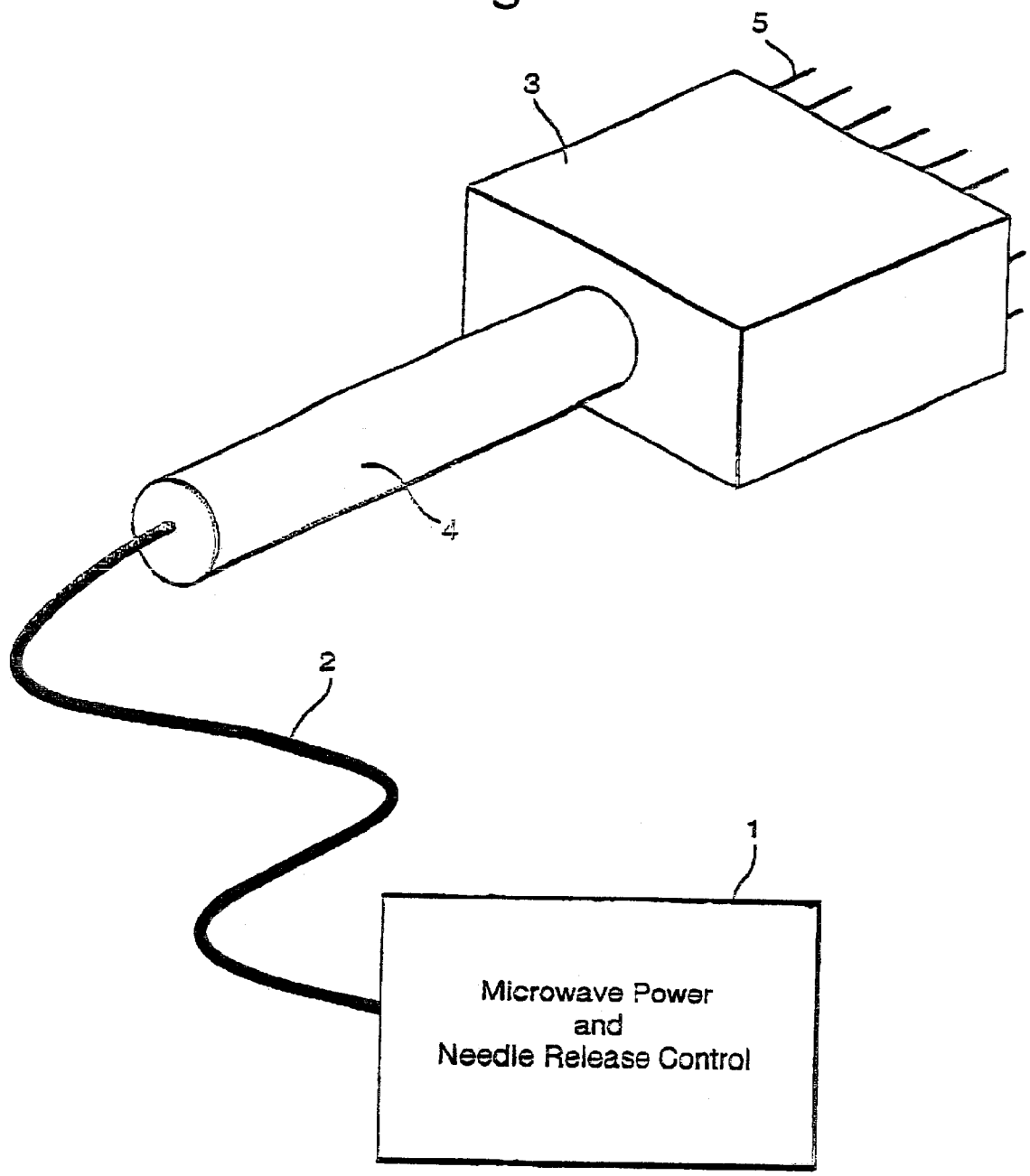
FIG. 1 is a schematic representation of an applicator in accordance with this invention.

Referring now to the drawings, a power and control unit (1) supplies up to 500 watts of microwave power via a coaxial cable (2) to a rectangular applicator (3). The head (3) has a handle (4) through which cable (2) passes, and an array (5) of retractable needles which are designed to provide precise irradiation of the tissue in the vicinity of the selected incision point. The unit (1) also contains a switching mechanism and control electronics to activate the release of the array of needles.

Figure 2:
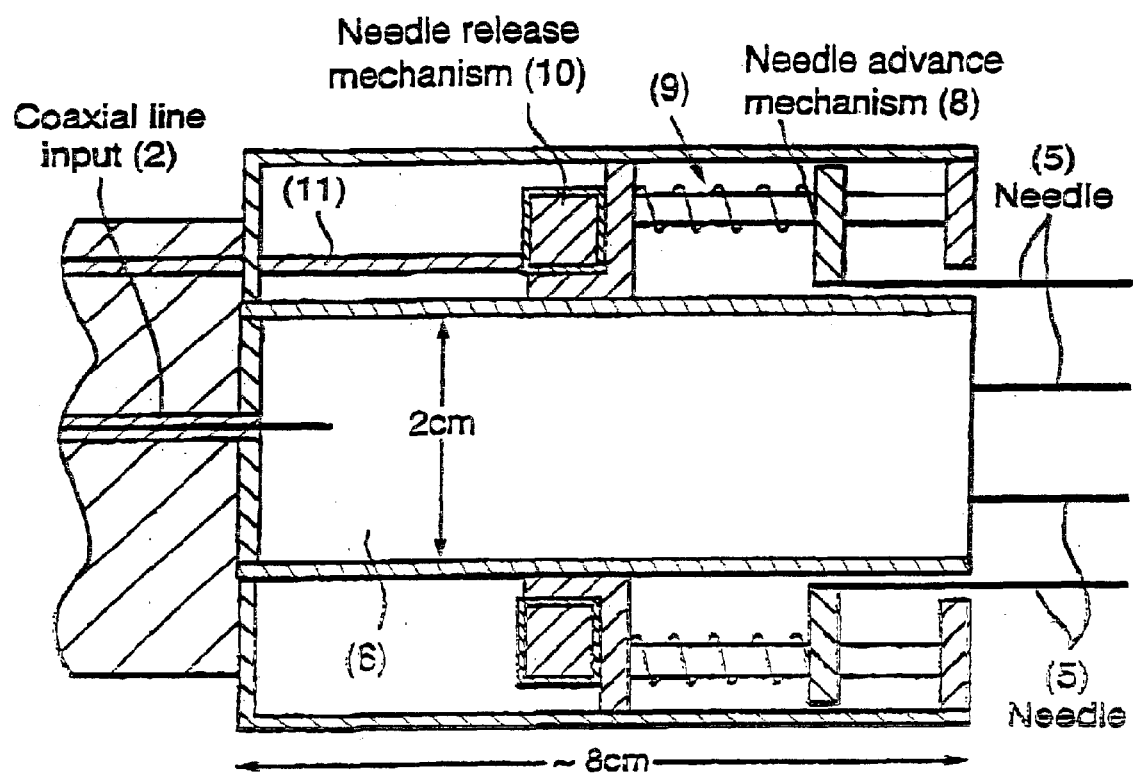
FIG. 2 is a cross-sectional view of the applicator head of FIG. 1.
Figure 3:
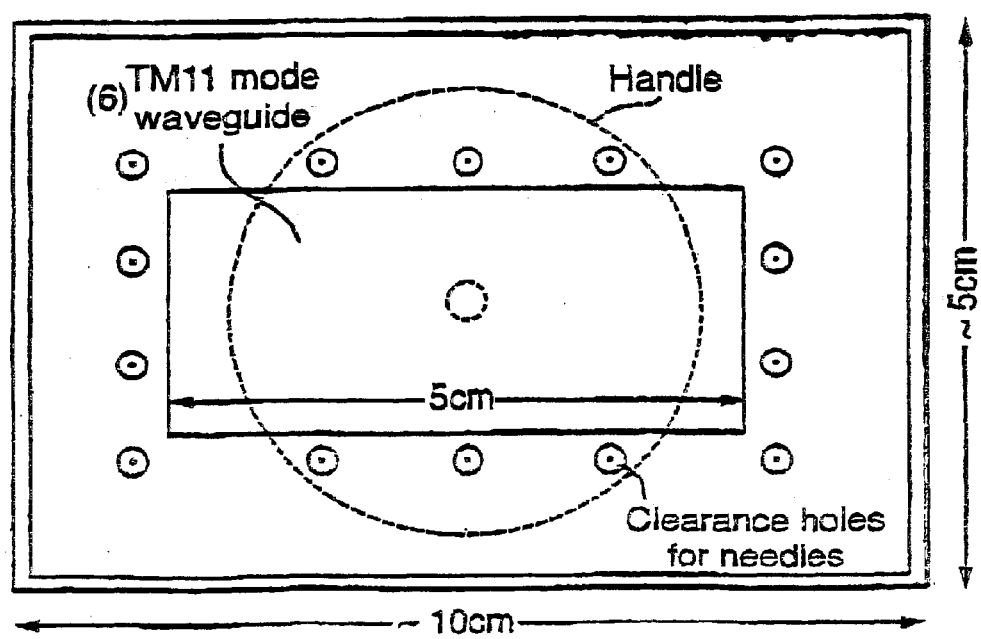
FIG. 3 is an end elevational view corresponding to FIGS. 1 and 2.

As shown in FIGS. 2 and 3, the applicator head (3) has a forward end face (6a). The applicator head (3) includes a rectangular waveguide (6) around the periphery of which the needles of array (5) are located in clearance holes (5a) (FIG. 3). The waveguide is a $TM_{11}$ mode waveguide and is filled with a suitable dielectric. For irradiation of a region 5 cm long by 2 cm wide, the rectangular waveguide should have corresponding dimensions and may be filled with a medium whose dielectric constant ($E_r$) is about 50. These parameters dictate that the microwave operating frequency should be of the order of 1 CHz. The specific values given here are by way of example only; it will be appreciated that a range of applicators designated to irradiate different volumes of tissue may be developed and these, of necessity, will have different dimensions and may require a different dielectric medium and a different operating frequency from that given above. In the illustrated embodiment, each of the needles is 3 cm long and made of steel. When the applicator is in operation, these needles will be advanced into the tissue where they function as an extension to the waveguide. A typical needle array may comprise about 20 needles. By employing a TM mode waveguide, leakage of energy through the "needle wall"—i.e., the area bounded by the array of needles—is kept to a low level (typically less than 10%).

FIG. 2 also shows a collar (8) to which each of the needles of the array (5) are secured. Collar (8) is acted upon by spring (9) which forms part of a solenoid mechanism (10) for controlling the advance and retraction of the array of needles. Power is supplied to the solenoid mechanism (10) via cable (11). As illustrated in FIG. 2, coaxial line (2) terminates within the dielectric-filled waveguide (6).

In operation, a surgeon will position the applicator head (3) against the region of tissue (e.g. liver) which is about to be incised. Initially the needle array (5) is retracted within head (3). When the applicator is actuated, solenoid mechanism (10) causes the needles of array (5) to be extended into the patient's tissue. Once they are embedded in the tissue, microwave energy at the desired frequency (e.g. 1 GHz) is supplied to waveguide (6) and passes therefrom into the volume of tissue enclosed by the array (5) of needles. Energy is supplied at a typical power level of 500 watts for a duration of about 15 secs when an applicator of the dimensions 5 cm×2 cm and a needle length of 3 cm is used. At the end of the treatment period, the microwave source is switched off and needle array (5) is retracted. The surgeon may then proceed with the incision and any subsequent procedures as may be necessary.

Blood loss from incision of tissue after heat treatment as described is greatly reduced in comparison to the results obtained in the absence of such heat treatment.

What is claimed is:

1. A device for generating localised heating in a selected body tissue, wherein said device comprises an applicator having a source of microwave radiation, the applicator being in the form of a waveguide for microwave radiation extending to one face of the applicator, and an array of retractable needles arranged so as to extend from said one face of the applicator; said one face of the applicator and the array of needles, when extended, defining a volume whose dimensions correspond to those of the tissue volume which is to be heated and the array of needles serving to confine the microwave energy field emanating from the waveguide for application to the volume of tissue to be heated.

2. A device as claimed in claim 1 wherein said waveguide is a rectangular waveguide around the periphery of which said array of retractable needles is positioned.

3. A device as claimed in claim 1 or 2 wherein said retractable needles are formed of steel.

4. A device as claimed in claim 1 wherein it comprises a needle advance mechanism including a collar to which the needles are secured.

5. A device as claimed in claim 4 wherein the movement of said collar is actuated by a solenoid mechanism.

* * * * *